(12) United States Patent
Goh et al.

(10) Patent No.: US 9,592,157 B2
(45) Date of Patent: Mar. 14, 2017

(54) SYSTEM AND METHOD FOR FEMTO-FRAGMENTATION OF A CRYSTALLINE LENS

(71) Applicants: Toh Seng Goh, Wildwood, MO (US); Brian D. McCary, Clayton, MO (US); David Haydn Mordaunt, Los Gatos, CA (US); Frieder Loesel, Mannheim (DE); Jochen Kandulla, Munich (DE); Gerhard Youssefi, Landshut (DE); Werner Banghard, Weilheim (DE)

(72) Inventors: Toh Seng Goh, Wildwood, MO (US); Brian D. McCary, Clayton, MO (US); David Haydn Mordaunt, Los Gatos, CA (US); Frieder Loesel, Mannheim (DE); Jochen Kandulla, Munich (DE); Gerhard Youssefi, Landshut (DE); Werner Banghard, Weilheim (DE)

(73) Assignees: BAUSCH & LOMB INCORPORATED, Rochester, NY (US); TECHNOLAS PERFECT VISION GMBH, Munich (DE)

( * ) Notice: Subject to any disclaimer, the term of this patent is extended or adjusted under 35 U.S.C. 154(b) by 279 days.

(21) Appl. No.: 13/795,641

(22) Filed: Mar. 12, 2013

(65) Prior Publication Data
US 2014/0135749 A1 May 15, 2014

Related U.S. Application Data

(60) Provisional application No. 61/724,729, filed on Nov. 9, 2012.

(51) Int. Cl.
*A61B 18/18* (2006.01)
*A61F 9/008* (2006.01)

(52) U.S. Cl.
CPC ...... *A61F 9/00812* (2013.01); *A61F 9/00825* (2013.01); *A61F 9/008* (2013.01);
(Continued)

(58) Field of Classification Search
CPC ............ A61F 9/008; A61F 2009/00872; A61F 9/00821; A61F 9/00804; A61F 2009/00887; A61F 2009/0087
(Continued)

(56) References Cited

U.S. PATENT DOCUMENTS 3,589,363 A 6/1971 Banko
3,805,787 A 4/1974 Banko
(Continued)

FOREIGN PATENT DOCUMENTS

WO 2007084694 A2 7/2007
WO 2008112294 A9 9/2008
WO 2009089504 A2 7/2009

OTHER PUBLICATIONS

Definition of Contiguous. Merriam-Webster Dictionary, retrieved on Oct. 1, 2015; Retrieved from the internet: <http://www.merriam-webster.com/dictionary/contiguous>.*
(Continued)

*Primary Examiner* — Lynsey Crandall
*Assistant Examiner* — Sebastian X Lukjan
(74) *Attorney, Agent, or Firm* — Nydegger & Associates

(57) ABSTRACT

A system and method for performing a femto-fragmentation procedure on tissue in the crystalline lens of an eye requires that a laser beam be directed and focused to a focal point in the crystalline lens of the eye. The focal point is then guided, relative to an axis defined by the eye, to create a segment cluster by causing Laser Induced Optical Breakdown (LIOB) of tissue in the crystalline lens. The resultant segment cluster includes a plurality of contiguous, elongated
(Continued)

segments in the crystalline lens that are individually tapered from an anterior end-area to a posterior end-area. Specifically, this is done to facilitate the removal of individual segments from the segment cluster in the crystalline lens.

13 Claims, 3 Drawing Sheets

(52) U.S. Cl.
CPC ....... *A61F 9/00804* (2013.01); *A61F 9/00821* (2013.01); *A61F 2009/0087* (2013.01); *A61F 2009/00872* (2013.01); *A61F 2009/00887* (2013.01); *A61F 2009/00897* (2013.01)

(58) Field of Classification Search
USPC ......................................................... 606/4–6
See application file for complete search history.

(56) References Cited

U.S. PATENT DOCUMENTS

| | | | |
|---|---|---|---|
| 4,428,748 A | 1/1984 | Peyman et al. | |
| 4,531,934 A | 7/1985 | Kossovsky et al. | |
| 4,538,608 A | 9/1985 | L'Esperance, Jr. | |
| 4,634,420 A | 1/1987 | Spinosa et al. | |
| 5,246,435 A | 9/1993 | Bille et al. | |
| 5,702,441 A | 12/1997 | Zhou | |
| 6,299,591 B1 | 10/2001 | Banko | |
| 6,322,556 B1 | 11/2001 | Gwon et al. | |
| 6,391,020 B1 | 5/2002 | Kurtz et al. | |
| 7,655,002 B2 * | 2/2010 | Myers | 606/5 |
| 7,863,543 B2 | 1/2011 | Bischoff et al. | |
| 8,187,168 B2 | 5/2012 | Wuchinich | |
| 2007/0173794 A1 | 7/2007 | Frey et al. | |
| 2007/0185475 A1 | 8/2007 | Frey et al. | |
| 2008/0039825 A1 * | 2/2008 | Lai | A61B 3/107 606/5 |
| 2009/0012507 A1 | 1/2009 | Culbertson et al. | |
| 2009/0149840 A1 | 6/2009 | Kurtz | |
| 2009/0171327 A1 | 7/2009 | Kurtz et al. | |
| 2009/0177189 A1 | 7/2009 | Raksi | |
| 2009/0299346 A1 * | 12/2009 | Bille et al. | 606/5 |
| 2010/0022995 A1 | 1/2010 | Frey et al. | |
| 2010/0042079 A1 | 2/2010 | Frey et al. | |
| 2010/0114079 A1 | 5/2010 | Myers et al. | |
| 2010/0137850 A1 | 6/2010 | Culbertson et al. | |
| 2010/0292678 A1 * | 11/2010 | Frey | A61F 9/008 606/5 |
| 2011/0184392 A1 | 7/2011 | Culbertson et al. | |
| 2011/0196350 A1 | 8/2011 | Friedman et al. | |
| 2011/0202044 A1 | 8/2011 | Goldshleger et al. | |
| 2012/0083774 A1 * | 4/2012 | Robl | A61F 9/009 606/5 |

OTHER PUBLICATIONS

PCT International Search Report, Application No. PCT/US20131066302, Oct. 23, 2013.
Conrad-Hebgerer, Effect of Femtosecond Laser Fragmentation of the Nucleus with Different Softening Grid Sizes on Effective Phaco Time in Cataract Surgery, J Cataract Refract Surg, vol. 38, Nov. 2012, pp. 1888-1894, Published by Elsevier Inc.

* cited by examiner

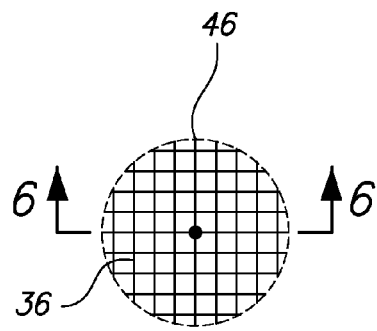
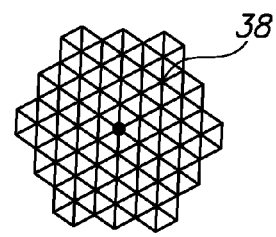
FIG. 4A  FIG. 4B
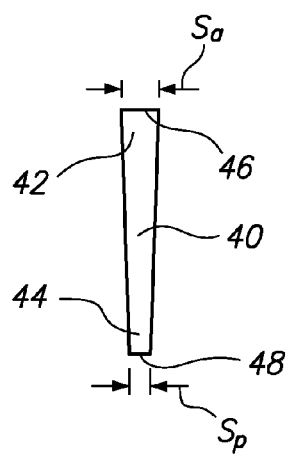
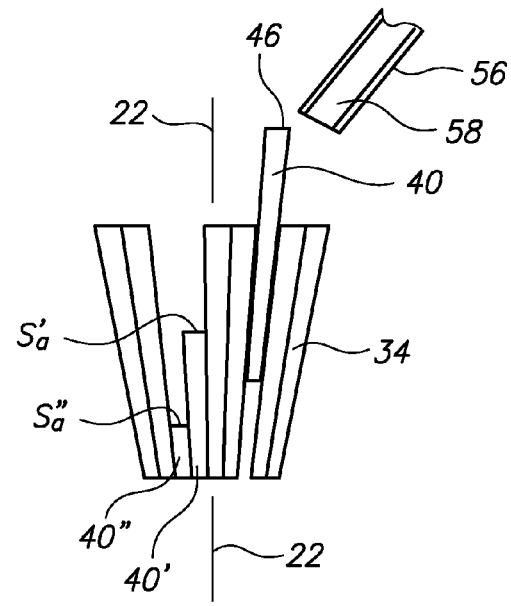
FIG. 5  FIG. 6

SYSTEM AND METHOD FOR FEMTO-FRAGMENTATION OF A CRYSTALLINE LENS

This application claims the benefit of U.S. Provisional Patent Application Ser. No. 61/724,729, titled SYSTEM AND METHOD FOR FEMTO-FRAGMENTATION OF A CRYSTALLINE LENS, filed Nov. 9, 2012. The entire contents of Application Ser. No. 61/724,729 are hereby incorporated by reference herein.

FIELD OF THE INVENTION

The present invention pertains generally to systems and methods for fragmenting the crystalline lens of an eye, prior to a lensectomy. More particularly, the present invention pertains to lens fragmentation procedures that employ a femtosecond laser to fragment the lens. The present invention is particularly, but not exclusively, useful for lens fragmentation procedures wherein a crystalline lens is fragmented into a plurality of contiguous, elongated segments that are individually tapered from an anterior end-area to a posterior end-area. In particular, this taper is employed to facilitate the removal of individual segments from the segment cluster during a lensectomy.

BACKGROUND OF THE INVENTION

With the increased use of electronic medical devices in surgical operations, the energy that is required to perform a surgical procedure has become a significantly more meaningful consideration. Furthermore, and perhaps most importantly, the clinical consequences of using excessive energy may have a significant effect on the surgical result. This is particularly so in the case of ophthalmic surgery where visual rehabilitation is of the utmost importance.

Within the general field of ophthalmic surgery, the concern here is specifically on cataract surgery. Conventional cataract surgery involves emulsification of the crystalline lens with an ultrasonic handpiece (a process known as "phacoemulsification") and aspiration of the emulsified lens from the eye. In this process the lens tissue that is to be removed is broken up into relatively small fragments (i.e. emulsified). The emulsified fragments are then aspirated from the lens capsule by, e.g., an aspiration needle. As a practical consideration, phacoemulsification can be a relatively time consuming task that requires the use of a substantial amount of ultrasonic energy.

In comparison with a typical application of ultrasonic energy, it is known that substantially less energy is required to perform Laser Induced Optical Breakdown (LIOB) on optical tissue. Moreover, LIOB can be accomplished with much greater precision. A consequence of this is that femtosecond lasers are now widely accepted for use in ophthalmic surgical procedures, increasingly including cataract surgery.

In a recent article entitled "Effect of Femtosecond Laser Fragmentation of the Nucleus with Different Softening Grid Sizes on Effective Phaco Time in Cataract Surgery," J Cataract Refract Surg., 2012, Ina Conrad-Hengerer, MD, et al. reported on energy considerations in cataract surgery. In this article they concluded that, in a pretreatment for cataract surgery (i.e. lens fragmentation), a femtosecond laser-assisted system which used a relatively smaller fragmentation grid (i.e. laser guidance pattern) resulted in a significantly lower phacoemulsification time (i.e. less energy requirements).

Given that fragmentation grid size is an important consideration in a pretreatment for cataract surgery, there are still additional considerations which can be addressed. In particular, the effect that fragment configuration may have on the efficacy of a lensectomy is still an open question. Further, the question as to how the resultant fragments may interact with, and possibly hinder, each other during the lensectomy is worth consideration.

In light of the above, it is an object of the present invention to provide a system and method for performing a femtosecond lens fragmentation (pretreatment) procedure, on tissue in the crystalline lens of an eye, which configures lens fragments to facilitate their removal from the lens during a lensectomy. Another object of the present invention is to provide a system and method for performing a femtosecond lens fragmentation (pretreatment) procedure which configures lens fragments in a manner that will minimize interactions between adjacent fragments that would otherwise hinder their removal from the lens during a lensectomy. Still another object of the present invention is to provide a system and method for performing a femtosecond lens fragmentation (pretreatment) procedure which is simple to implement and is relatively cost effective.

SUMMARY OF THE INVENTION

In accordance with the present invention, a system and method are disclosed for performing a femto-fragmentation procedure on tissue in the crystalline lens of an eye. As envisioned for the present invention, this lens fragmentation procedure is to be accomplished prior to a lensectomy in cataract surgery. In particular, the present invention employs a femtosecond laser system to perform lens fragmentation, and it results in the creation of individual lens segments that are each uniquely tapered to facilitate their removal from a crystalline lens during the lensectomy.

Structurally, the system of the present invention includes a laser unit for generating a femtosecond laser beam. The laser unit also includes the necessary optics to direct the laser beam from the laser unit along a beam path, to a focal point in the crystalline lens of the eye. Additionally, the system includes a computer/controller which is connected with the laser unit for guidance and control purposes. Further, the computer/controller is used to generate a specific template pattern that will be used by the system to guide the laser beam. Within this combination, the beam path and the focal point are both established relative to an axis that is defined by the eye, and they are guided in accordance with the template pattern. For purposes of the present invention, the axis may be an optical axis of the eye.

In an operation of the present invention, the focal point of the laser beam is guided in accordance with the template pattern to cause a Laser Induced Optical Breakdown (LIOB) of tissue in the crystalline lens. The consequence here is the creation of a segment cluster in the crystalline lens of the eye that contains a plurality of contiguous segments. In detail, each segment in the segment cluster individually extends between an anterior end-area, and a posterior end-area. Specifically, the anterior end-area is characterized by a dimension "$s_a$", and the posterior end-area is characterized by a corresponding dimension "$s_p$". It is an important aspect of the present invention that each segment is tapered from the anterior end-area of the segment toward the posterior end-area ("$s_a$">"$s_p$"). Operationally, this is done to facilitate a subsequent removal of the segment from the crystalline lens.

In line with the above discussion, guidance of the laser beam by the computer/controller will be accomplished using a computer-generated template pattern that is oriented substantially perpendicular to the axis. Depending on the particular template pattern that is used (e.g. rectangular, or triangular, or other), there will be consequent variations in the configuration of the individual segments that are created. Preferably, however, the template pattern will create an anterior end-area for each segment that is shaped as a rectangle (e.g. a square), and the characteristic dimension "$s_a$" of the anterior end-area will be a side distance of the rectangle. In most instances, the characteristic dimension "$s_a$" is preferably less than approximately three hundred and fifty microns ($s_a$<350 μm). As envisioned for the present invention, the characteristic dimension "$s_p$" of the posterior end-area will normally be less than ninety percent of the characteristic dimension "$s_a$" of the anterior end-area ($s_p$<0.9$s_a$). The length of each segment will be about 4 mm or 80% of the actual lens thickness.

For safety reasons, the method of the present invention will be preferably accomplished within a predetermined volume of tissue inside the crystalline lens. For instance, this predetermined volume of tissue may be established to be more than a selected distance (e.g. 50 μm) from the exterior surface of the crystalline lens. Such a safety margin may be most important with regard to the posterior capsule.

During a lensectomy, it is envisioned that each segment will be individually removed (aspirated) from the segment cluster. With this in mind, the dimension "$s_a$" for the anterior end-area is established so that the segment can be received (i.e. accommodated) and removed by a phaco-needle. Further, the taper that is established for each segment is intended to minimize, or eliminate, any interaction that might otherwise occur with adjacent segments as a particular segment is being removed (aspirated).

In another embodiment, it is envisioned that each segment will be individually removed (aspirated) from the posterior of the lens. For this embodiment, a segment cluster is created in the crystalline lens of the eye that contains a plurality of contiguous segments, as described above, but with each segment tapered from the posterior end-area of the segment toward the anterior end-area ("$s_a$" <"$s_p$"). Operationally, this is done to facilitate a subsequent removal of the segment from the posterior of the crystalline lens.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 4A is a plan view of a template having a pathway pattern for guiding a laser beam in accordance with the present invention;

FIG. 4B is a plan view of an embodiment of another template having an alternate pathway pattern for guiding a laser beam in accordance with the present invention;

FIG. 5 is a side elevation view of a lens segment that would be created in accordance with the present invention using a template as shown in FIG. 4A;

FIG. 6 is a side elevation view, in cross section, of a segment cluster, as would be seen along the line 6-6 in FIG. 4A, with portions of segments already removed and with another individual segment in the process of being removed from the cluster during a lensectomy;

DESCRIPTION OF THE PREFERRED EMBODIMENTS

Figure 1:
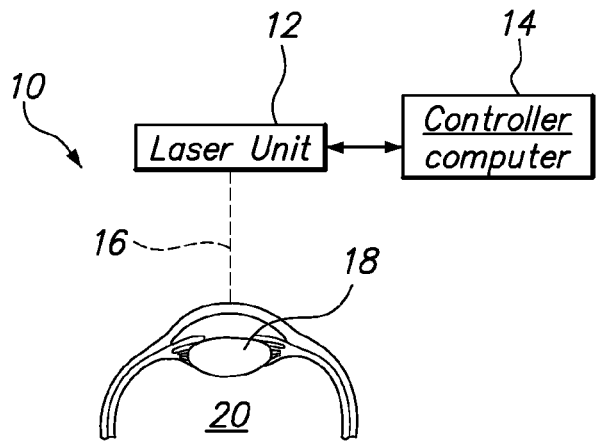
FIG. 1 is a schematic view of the components of the system for the present invention.

Referring initially to FIG. 1, a system in accordance with the present invention is shown and is generally designated 10. As shown, the system 10 essentially includes a laser unit 12 and a controller/computer 14. In combination, the computer/controller 14 is connected with the laser unit 12 for the purposes of guiding and controlling the movement of a laser beam 16 that is generated and focused by the laser unit 12. Necessarily, the laser unit 12 is of a type that generates a pulsed laser beam 16 which is capable of performing Laser Induced Optical Breakdown (LIOB) on anatomical tissue. Preferably, the laser beam 16 will have laser pulses with pulse durations in the femtosecond range.

As indicated in FIG. 1, the system 10 of the present invention is primarily intended to be used for ophthalmic operations on the crystalline lens 18 of an eye 20. More specifically, the present invention envisions a use for the laser unit 12 that involves breaking-up, or fragmenting, the crystalline lens 18 in preparation for a subsequent lensectomy. When a femtosecond laser is used for such a purpose (i.e. laser unit 12), the operation is often referred to as a "femto-fragmentation" procedure.

Figure 2:
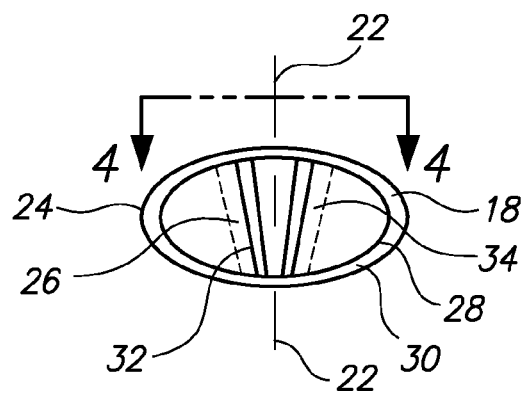
FIG. 2 is a profile view of a crystalline lens.

In an operational context for the present invention, as shown in FIG. 2, an axis 22 is defined by the crystalline lens 18. As a practical matter, the axis 22 will be established as a reference datum for the system 10 and it may conveniently be based on a selected optical axis of the eye 20. Also, the crystalline lens 18, itself, has an exterior surface 24 that acts as a reference datum. With these data in mind, a tissue volume 26, which is located inside the crystalline lens 18, is diagnostically identified for lens fragmentation during a lensectomy. For safety reasons, the tissue volume 26 may be located generally within a boundary 28 that is clinically identified to establish a safety margin 30.

In general, FIG. 2 shows that the tissue volume 26 will be centered on the axis 22, and it will be oriented substantially symmetric with the axis 22. Further, the safety margin 30 which surrounds the tissue volume 26 will typically be at least fifty microns in depth. Within the defined tissue volume 26, cuts 32 can then be made into the crystalline lens 18, inside the safety margin 30, by the laser unit 12. As indicated above, these cuts 32 into tissue of the crystalline lens 18 will result from a Laser Induced Optical Breakdown (LIOB) of the tissue which occurs at the focal point of the laser beam 16.

Figure 3:
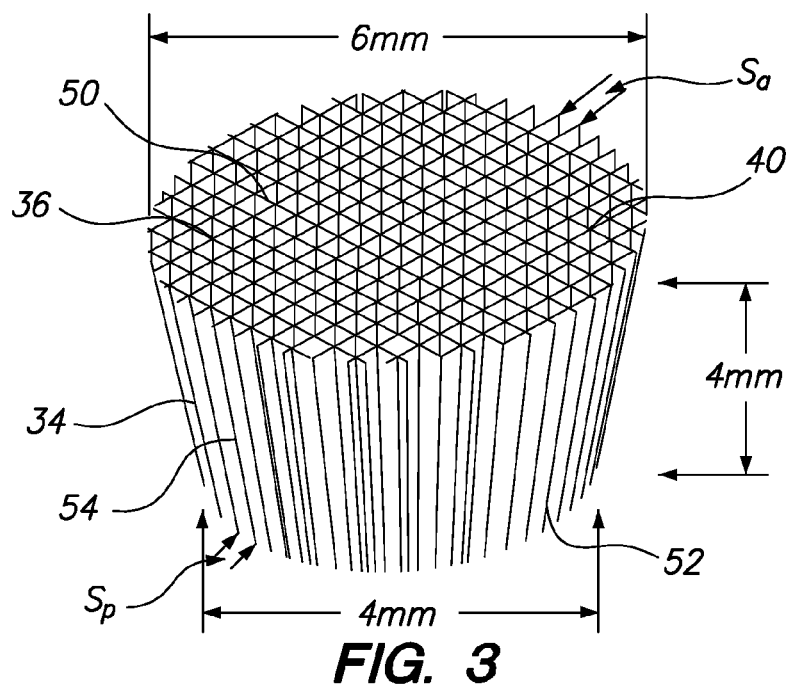
FIG. 3 is a perspective view of a segment cluster as would be created inside the crystalline lens of an eye in accordance with the present invention.

In accordance with the present invention, the cuts 32 into the crystalline lens 18 are made to create a segment cluster 34, such as the one shown in FIG. 3. In particular, a segment cluster such as the segment cluster 34 results when the laser beam 16 that is generated by the laser unit 12 is moved in accordance with a template pattern 36 shown in FIG. 4A. In each case, it is to be appreciated that other template patterns can be used for the same purpose. For instance, the pattern 38 that is shown in FIG. 4B is an example of such an alternate template pattern. With this in mind, the particular configuration for a segment cluster 34 will depend on the pattern that is used (e.g. template pattern 36 for squares and template pattern 38 for triangles). Typically, as implied above, these patterns 36/38 will be computer-generated by the controller/computer 14.

In detail, the segment cluster 34 that is shown in FIG. 3 includes a plurality of contiguous individual segments 40 (i.e. rods), which are each essentially equivalent to the exemplary segment 40 shown in FIG. 5. In this plurality, each segment 40 (rod) is elongated, and each has an anterior end 42 and a posterior end 44. Further, for the exemplary segment 40, the anterior end 42 of the segment 40 will be in the shape of a square that defines an anterior end-area 46 (see FIG. 4A). Importantly, this end-area 46 will have a dimension "$s_a$" that is characteristic of its shape. In the example presented here for discussion, the dimension "$s_a$" is the length of a side of the square, anterior end-area 46. It should also be noted that the segment 40 has a posterior end-area 48 which is located at its posterior end 44. This posterior end-area 48 is also square shaped, and its characteristic dimension, which corresponds with the dimension "$s_a$", is the dimension identified as "$s_p$". The present invention, however, envisions there may be shape differences between the anterior end-area 46 and the posterior end-area 48, as well as size and dimension differences.

An important structural aspect of each segment 40 is that it is tapered in the posterior direction. Thus, the end-area 46 of segment 40 is greater than the end-area 48. A consequence of this is that the segment cluster 34, itself, will also be tapered. A functional purpose for this structural configuration is to facilitate a separation between adjacent segments 40 when they are individually pulled in an anterior direction.

Returning to FIG. 3, exemplary dimensions for the segment cluster 34, and thus for the segments 40 also, are indicated. In particular, the segment cluster 34 is shown to be around 6 mm across its anterior surface 50, and around 4 mm across its posterior surface 52. Thus, in this case, "$s_a$" of the anterior end-area 46 may be around half again as long as "$s_p$" for the posterior end-area 48 of the segment 40 ($s_a \sim 1.5 s_p$). FIG. 3 also indicates that "$s_a$" for the anterior end-area 46 of each segment 40 (rod) will preferably be around three hundred and fifty, microns (350 µm). As also indicated, the length of each segment 40 may be about as long as the side 54 of the segment cluster 34 (e.g. approximately 4 mm or 80% of lens thickness). These dimensional relationships, of course, are only exemplary. The physical size of the crystalline lens 18, and the diagnostic evaluation of the crystalline lens 18, will significantly contribute to a determination of these dimensions for the segment 40. In general, however, the characteristic dimension "$s_p$" of the posterior end-area 48 is preferably less than ninety percent of the corresponding characteristic dimension "$s_a$" of the anterior end-area 46 ($s_p < 0.9 s_a$).

In FIG. 6, the removal of a segment 40 from a segment cluster 34, as envisioned for the present invention, is operationally depicted during a lensectomy. Specifically, as shown, a phaco-needle 56 is being used to aspirate the segment 40. In this operation it is important that the lumen 58 of the phaco-needle 56 be dimensioned to receive the segment 40. In particular, it is necessary that the dimension "$s_a$" for the anterior end-area 46 of the segment 40 be such that the lumen 58 is able to accommodate the anterior end-area 46 of the segment 40. With such an accommodation, the segment 40 can be removed from the segment cluster 34.

Importantly, as disclosed above, the segment 40 is appropriately tapered to facilitate its removal from the segment cluster 34. Although entire segments 40 may be removed intact, the segments 40' ($s_a$') and 40" ($s_a$") are shown in FIG. 6 to illustrate the fact that partial segments 40' and 40" may sometimes result during a lensectomy. Specifically, this may happen because there are so-called "fracture planes" within the crystalline lens 18, along which tissue of the crystalline lens 18 may be weak and subject to separation. Operationally, these fracture planes may be further weakened by the LIOB of adjacent tissue during lens fragmentation. In the event, the fracture lines will typically align substantially perpendicular to the axis 22, and thereby further facilitate the removal of segments 40. Regardless, the consequence of this is that shorter segments 40' and 40" and complete segments 40 can be removed with similar ease.

Figure 7:
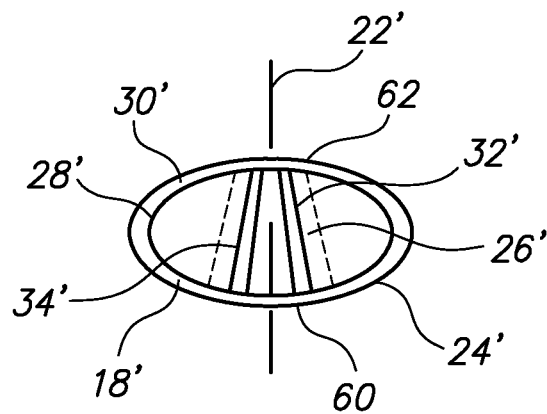
FIG. 7 is a profile view of a crystalline lens showing an incision pattern for creating a segment cluster to facilitate removal of lens material from the posterior of the lens.

FIG. 7 shows another implementation in which a crystalline lens 18' is incised to create a segment cluster 34' to facilitate removal of lens material from the posterior of the crystalline lens 18'. As shown in FIG. 7, an axis 22' is defined by the crystalline lens 18' that can be used to establish a reference datum and the crystalline lens 18' has an exterior surface 24' that can also act as a reference datum. Also, crystalline lens 18' includes a posterior side 60 and an anterior side 62. In addition, as shown, a tissue volume 26' is located inside the crystalline lens 18' that can be diagnostically identified for lens fragmentation during a lensectomy. As discussed above, the tissue volume 26' may be located generally within a boundary 28' that is clinically identified to establish a safety margin 30'.

Continuing with FIG. 7, it can be seen that the tissue volume 26' can be centered on the axis 22', and can be oriented substantially symmetric with the axis 22'. Within the tissue volume 26', cuts 32' can then be made into the crystalline lens 18' and inside the safety margin 30' by the laser unit 12 (FIG. 1). As indicated above, these cuts 32' into tissue of the crystalline lens 18' can result from a Laser Induced Optical Breakdown (LIOB) of the tissue which occurs at the focal point of the laser beam 16 (FIG. 1).

Figure 8:
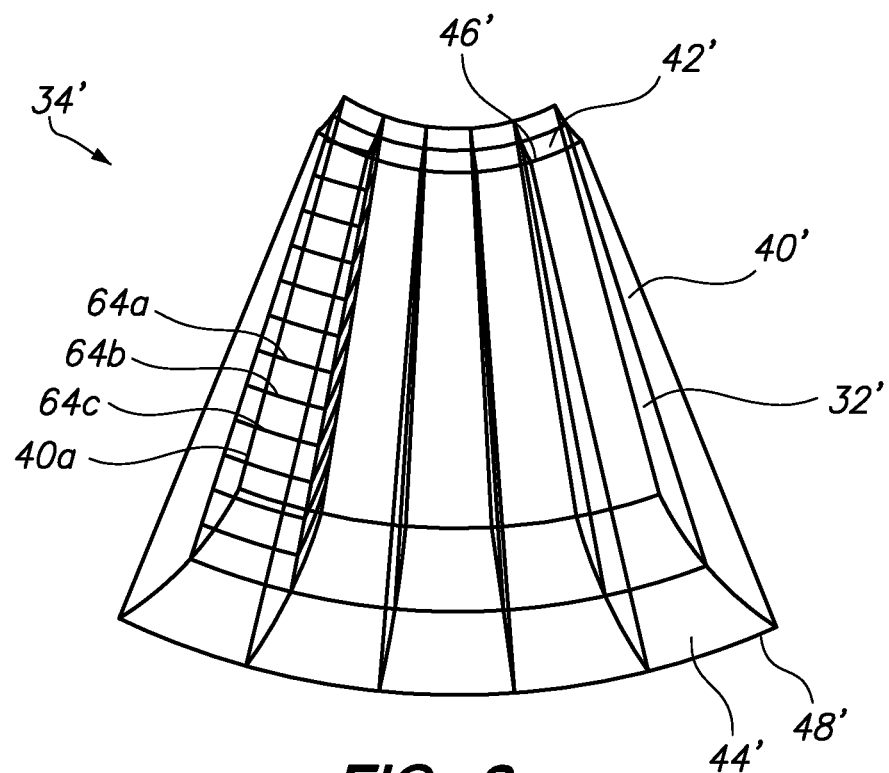
FIG. 8 is a perspective view of a segment cluster as would be created inside the crystalline lens of an eye in accordance with the present invention to facilitate removal of lens material from the posterior of the lens.

As best seen in FIG. 8, the cuts 32' into the crystalline lens 18' (FIG. 7) can be patterned to create a segment cluster 34'. More specifically, the segment cluster 34' can be achieved when the laser beam 16 (FIG. 1) that is generated by the laser unit 12 is moved in accordance with a template pattern for squares, rectangles, or triangles (as discussed above). FIG. 8 shows LIOB paths (of which LIOB paths 64a-c are labeled) to create the segment 40a.

Continuing with FIG. 8, it can be seen that the segment cluster 34' includes a plurality of contiguous individual segments 40' (i.e. elongated rods) with each segment 40' having an anterior end 42' and a posterior end 44'. Further, for the exemplary segments 40' shown, the anterior end 42' of the segment 40' can be in the shape of an arcuate sided rectangle that defines an anterior end-area 46'. For the segments 40' shown, the end-area 46' will have a dimension "$s_a$" that is characteristic of its shape and size. For example, the dimension "$s_a$" can be calculated as the area of the arcuate sided rectangle. FIG. 8 also shows that the segment 40' has a posterior end-area 48' which is located at its posterior end 44'. This posterior end-area 48' is also shaped as an arcuate sided rectangle, and its characteristic dimension, which corresponds with the dimension "$s_a$" is the dimension identified as "$s_p$". The present invention, however, envisions there may be shape differences between the anterior end-area 46' and the posterior end-area 48', as well as size and dimension differences.

For the embodiment illustrated by FIGS. 7 and 8, each segment 40' is tapered in the anterior direction. Thus, the end-area 48' of segment 40' is greater than the end-area 46' (i.e. $s_p > s_a$). A consequence of this is that the segment cluster 34', itself, will also be tapered. A functional purpose for this structural configuration is to facilitate a separation between adjacent segments 40' when they are individually pulled in a posterior direction.

While the particular System And Method For Femto-Fragmentation Of A Crystalline Lens as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for performing a femto-fragmentation lensectomy procedure on tissue in the crystalline lens of an eye which comprises the steps of:
    orienting a laser unit to direct a laser beam along a beam path to a focal point in the crystalline lens of the eye, wherein the lens defines an axis and the beam path and the focal point are established relative to the axis defined by the lens;
    guiding the focal point of the laser beam with reference to the axis to cause a Laser induced Optical Breakdown (LIOB) of tissue in the crystalline lens at the focal point;
    creating a plurality of contiguous, elongated, segments in the crystalline lens during the guiding step, wherein each segment is aligned axially in the lens and individually extends between a respective anterior end-area characterized by a dimension "$s_a$", and a respective posterior end-area characterized by a corresponding dimension "$s_p$", and wherein each segment is tapered from the anterior end-area toward the posterior end-area ("$s_a$">"$s_p$"); and
    aspirating segments from the creating step, to remove the created segments of the crystalline lens from the eye.

2. A method as recited in claim 1 further comprising the steps of:
    generating a template pattern, wherein the template pattern is oriented relative to the reference datum; and
    moving the beam path of the laser beam in accordance with the template pattern during the guiding step.

3. A method as recited in claim 1 wherein the anterior end-area is shaped as a rectangle and the characteristic dimension "$s_a$" of the anterior end-area is a side distance of the rectangle.

4. A method as recited in claim 3 wherein the anterior end-area is a square.

5. A method as recited in claim 4 wherein the characteristic dimension "$s_a$" is less than three hundred and fifty microns ($s_a < 350$ μm).

6. A method as recited in claim 1 wherein the anterior end-area is shaped as a triangle.

7. A method as recited in claim 1 wherein the characteristic dimension "$s_p$" of the posterior end-area is less than ninety percent of the characteristic dimension "$s_a$" of the anterior end-area ($s_p < 0.9 s_a$).

8. A method as recited in claim 1 wherein the crystalline lens has an exterior surface, and the creating step is accomplished within a predetermined volume of tissue in the crystalline lens, wherein the predetermined volume of tissue is more than a selected distance from the exterior surface of the crystalline lens to establish a safety margin therebetween.

9. A method as recited in claim 8 wherein the safety margin is greater than approximately 50 microns.

10. A method for performing a femto-fragmentation lensectomy procedure on a transparent material in an eye which comprises the steps of:
    orienting a laser unit to direct a laser beam along a beam path to a focal point in the transparent material, wherein the beam path and the focal point are established relative to an axis defined defined by the transparent material;
    guiding the focal point of the laser beam with reference to the axis to photoablate transparent material at the focal point;
    creating a plurality of contiguous, elongated, segments in the transparent material during the guiding step, wherein each segment is aligned axially in the lens and individually extends between a respective anterior end-area characterized by a dimension "$s_a$", and a respective posterior end-area characterized by a corresponding dimension "$s_p$", and wherein each segment is tapered from the anterior end-area toward the posterior end-area ("$s_a$">"$s_p$"); and
    aspirating segments resulting from the creating step, to remove the created segments of the transparent material from the eye.

11. A method as recited in claim 10 further comprising the steps of:
    generating a template pattern;
    orienting the template pattern relative to the reference datum; and
    moving the beam path of the laser beam in accordance with the template pattern during the guiding step.

12. A method as recited in claim 10 wherein the anterior end-area is shaped as a rectangle and the characteristic dimension "$s_a$" of the anterior end-area is a side distance of the rectangle, and wherein the characteristic dimension "$s_a$" is less than three hundred and fifty microns ($s_a < 350$ μm).

13. A method as recited in claim 10 wherein the characteristic dimension "$s_p$" of the posterior end-area is less than ninety percent of the characteristic dimension "$s_a$" of the anterior end-area ($s_p < 0.9 s_a$).

* * * * *